United States Patent [19]

Carraher, Jr. et al.

[11] Patent Number: 5,043,463

[45] Date of Patent: Aug. 27, 1991

[54] NOVEL COMPOUNDS FOR THE CONTROL OF MICROORGANISMS

[75] Inventors: Charles E. Carraher, Jr., Parkland; Cindy Butler, Boca Raton, both of Fla.

[73] Assignee: Florida Atlantic University, Boca Raton, Fla.

[21] Appl. No.: 569,099

[22] Filed: Aug. 17, 1990

[51] Int. Cl.$^5$ .............................................. C07F 7/22
[52] U.S. Cl. ........................................ 556/88; 556/87; 556/89
[58] Field of Search ................... 556/88, 89, 87, 105, 556/94; 514/493

[56] References Cited

U.S. PATENT DOCUMENTS

| | | | |
|---|---|---|---|
| 2,626,953 | 1/1953 | Mack et al. | 556/89 |
| 3,806,530 | 4/1974 | Dorfelt et al. | 556/105 X |
| 4,390,640 | 6/1983 | Rasshofer et al. | 556/89 X |
| 4,546,109 | 10/1985 | Hubele et al. | 514/493 |
| 4,795,820 | 1/1989 | Synoradzki et al. | 556/88 X |

OTHER PUBLICATIONS

Carraher, C., and J. Piersman (1973) "Modification of Poly(vinyl alcohol) Through Reaction With Tin Reactions," Die Angewandte Makromolekulare Chemie 28:153–160.

*Primary Examiner*—Arthur C. Prescott
*Attorney, Agent, or Firm*—Saliwanchik & Saliwanchik

[57] ABSTRACT

The subject invention concerns novel compounds and methods for inhibiting the growth of microorganisms. Specifically, tin-containing polymers which are selectively active against *Candida albicans* are described. The invention further concerns a unique process for synthesizing the novel compounds.

16 Claims, No Drawings

NOVEL COMPOUNDS FOR THE CONTROL OF MICROORGANISMS

BACKGROUND OF THE INVENTION

The modification of poly(vinyl alcohol) (PVA) has previously been reported. As early as 1973 we reported the modification of PVA through reaction with specific organostannane halides (Carraher, C. and J. Piersman, (1973) Die Angewandte Makromolekulare Chemie, 28, 153). The products thus produced are crosslinked and insoluble when organostannane dihalides are used but they are linear when the monohalide is employed. Much of this work was based on the idea that organometallics such as organostannane halides act as electrophiles for attack by Lewis bases such as hydroxyl-containing compounds.

Polymeric organic tin compounds are also described in U.S. Pat. No. 2,626,953 issued to Mack et al.

The compounds reported by Carraher and Piersman in their 1973 paper are organostannane compounds where butyl and phenyl groups have been included into the polymer. Originally only the dibutyl, tributyl, diphenyl, and triphenyl stannanes were successfully included within the PVA. Carraher and Piersman reported that their efforts to react PVA with certain methyl and propyl organostannane halides were not successful. No biological activity was reported, or even suggested, by Carraher and Piersman for the organostannane polymers which they prepared or by Mack et al. in their patent for polymeric organic tin compounds though it is generally known that some tin-containing compounds may exhibit biological activity.

Yeast infections are among the most common to mankind. Microbes of the genus Candida are normal inhabitants of the bowel. These microbes are also found on the skin and in sputum of healthy individuals. *Candida albicans* is by far the most pathogenic member of the Candida family. Serious infections associated with it occur: after extensive surgergy, with AIDS debilitation, leukemia and lymphoma. All of these conditions produce a decreased immune response, setting the stage for Candida pathogenesis.

Candida also causes vulvovaginitis, meningitis, pulmonary candidiasis, thrush, and endocarditis. It is most often remembered, however, as the organism that is responsible for vaginal yeast infections in women. This condition occurs most frequently, and with greater severity, in areas where the climate is warm and moist. It often follows antibiotic therapy and is difficult to eradicate.

BRIEF SUMMARY OF THE INVENTION

The subject invention concerns novel compounds and the use of these compounds to control the growth of microorganisms. The novel compounds are poly(vinyl alcohols) (PVA) which have been modified with organostannane compounds using a special process. This process utilizes "poorer" solvents which facilitate the production of modified tin-containing PVA compounds having methyl, ethyl, and propyl moieties. The novel compounds have been found to effectively inhibit the growth of Candida microorganisms. Advantageously, and surprisingly, the inhibition of Candida is selective: other microbes are inhibited to a much lesser extent or not at all.

The ability of the novel compounds to selectively control *Candida albicans* make these compounds particularly useful for the control of yeast infections. Using these compounds, the growth of pathogenic Candida microbes can be inhibited without killing desirable microbes. Thus, the delicate positive microfloral balance of the infected site is not substantially disturbed.

DETAILED DESCRIPTION OF THE INVENTION

The subject invention relates to novel tin-containing PVA's and the use of these compounds to inhibit the growth of microorganisms. By utilizing a special synthetic process, PVA's with mono-, di-, and trialkyl moieties have been produced. It has been discovered that when the alkyl group is methyl, ethyl, or propyl, the resulting modified PVA shows high activity against *Candida albicans*. Advantageously, this activity is selective and, thus, it is possible to eradicate the pathogenic *Candida albicans* without destroying desirable micorflora.

The invention further concerns a synthetic process for preparing the novel compounds. Specifically, it was discovered that by carrying the reaction out using an organic liquid in which the organostannane is poorly soluble it is possible to produce PVA compounds having methyl, ethyl, and propyl moieties. The solvents used can be $CHCl_3$, $CCl_4$, or other suitable largely nonpolar solvents in which the organostannane is barely dissolved.

Also, the compounds of the subject invention can be combined with a plasticizing agent. The plasticizing agent may be, for example, dialkyl phthalate, isodocyl diphenylphosphate, or dioctyl sebocate. The use of these agents can make handling of the compounds easier without decreasing the biological activity.

MATERIALS AND METHODS

Commerical PVA (99% hydrolyzed, Aldrich, Milwaukee, WI) was employed along with the organostannane halides (from Aldrich) as received. A variety of molecular weight PVA's are available and may be used according to the subject invention.

An aqueous solution of PVA containing sodium hydroxide was used. The amount of sodium hydroxide may be, for example, equal to the theoretical maximum mole amount of chloride (or other halide) available from the organostannane halide. Stirring (about 18,000 rpm, no load) was begun and the organic solution (generally carbon tetrachloride or chloroform) containing the organostannane halide added. Virtually any method of addition may be used. For example, the organostannane halide may be added rapidly at room temperature. The product rapidly precipitates from the reaction mixture, is collected by suction filtration, washed repeatedly with water, transferred to a glass petri dish and dried. When a plasticizer was used, it was added to the organic phase prior to the reaction. For example, 2 ml of a plasticizer could be used.

Thermogravimetric analysis was conducted employing a duPont TGA while differential scanning calorimetry was carried out using a duPont 900 DSC cell. Infrared spectra were obtained using films employing a Nicolet 5DX-FTIR. Mass spectral analysis was carried out by the Nebraska Mass Spectrometry Service Laboratory. Analysis was carried out using a direct insertion probe connected to a Kratos MS-50 mass spectometer operating in the E.I. mode, 8 kr acceleration and 10 sec/decade scan rate with a probe temperature to 450° C.

Following are examples which illustrate procedures, including the best mode, for practicing the invention. These examples should not be construed as limiting. All percentages are by weight and all solvent mixture proportions are by volume unless otherwise noted.

EXAMPLE 1

Structural Properties of Novel Compounds

Using the methods described above, it is possible to effect the reaction of organostannane halides where the R groups may be methyl, ethyl, or propyl. Other R groups such as butyl and phenyl can also be prepared. Infrared study of the products is consistent with a product containing units such as (1), (2), and (3) below:

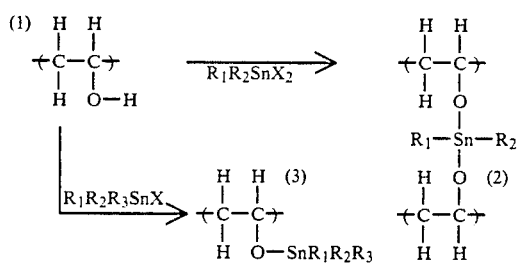

For the structures shown below, $R_1$, $R_2$, and $R_3$ may be the same or different. The Sn-O-R asymmetric stretch is found around 670 (all bands are given in $cm^{-1}$) while the Sn-O-R symmetric stretch is found about 600 and 570. For products derived from aliphatic organostannane bands characteristic of the aliphatic portion and C-H stretching in the PVA are present in the 2900 to 3000 region.

The mass spectra of the products are consistent with structures as described by (1)-(3). Table 2 contains the major ions derived from the condensation product of PVA and dipropyltin dichloride. Smaller ion fragments are derived from the propyl moieties and the fragmented PVA backbone. Higher ion fragments (>150 Daltons) have tin present. Table 1 contains a listing of the percentage of the major isotopes naturally found. There is a good agreement between the percentage natural abundance of the various tin isotopes and that found in the fragmentation of the product.

Similar results are found for the condensation product of PVA and dimethyltin dichloride. Table 3 contains assigments for the most abundant ion fragments. Again, there are numerous ion fragments containing tin present in the predicted isotope abundance. Tables 4 and 5 contain such results for the SnMe and $OSnMe_2$ units.

TABLE 1

| Percentage Natural Abundance of Tin Isotopes. | | | |
|---|---|---|---|
| Tin Isotope | % Natural Abundance | Tin Isotope | % Natural Abundance |
| 116 | 14.0 | 120 | 33.0 |
| 117 | 7.7 | 122 | 4.7 |
| 118 | 24.0 | 124 | 6.0 |
| 119 | 8.7 | | |

TABLE 2

Major (1% and greater) Ion Fragments for the Condensation product of PVA and Dipropyltin Dichloride.

| Daltons (m/e) | % Relative Abundance | (Possible) Assignments |
|---|---|---|
| 39 | 4.9 | $C_3H_3$ |
| 40 | 6.6 | $C_3H_4$ |
| 41 | 8.0 | $C_3H_5$ |
| 42 | 2.5 | $C_3H_6$ |
| 43 | 7.0 | Pr, $C_2H_2OH$ |
| 44 | 5.0 | $CO_2$, $CH_2CHOH$ |
| 55 | 3.8 | $C_3H_2OH$, $C_6H_7$ |
| 56 | 2.0 | $C_3H_3OH$ |
| 57 | 3.0 | $C_3H_4OH$ |
| 65 | 1.3 | $C_5H_5$ |
| 66 | 1.4 | $C_5H_6$ |
| 69 | 2.8 | $C_4H_4OH$ |
| 70 | 1.9 | $C_4H_5OH$ |
| 94 | 4.0 | $C_5H_{10}(OH)_2$ |
| 159 | 1.1 | $OSnMe_2$ |
| 161 | 1.5 | $OSnMe_2$ |
| 163 | 2.0 | $C_3H_4OSnPr$ |
| 223 | 1.2 | $C_3H_4OSnPr$ |
| 225 | 2.1 | $C_6H_6SnPr$ |
| 241 | 1.1 | $C_6H_6SnPr$ |

TABLE 3

Major (10% and greater) Ion Fragments Derived From the Condensation of Dimethyltin Dichloride and PVA.

| Daltons (m/e) | % Relative Abundance | (Possible) Assignments |
|---|---|---|
| 39 | 11 | $C_3H_3$ |
| 41 | 16 | $C_3H_5$ |
| 44 | 30 | $CO_2$, $CH_2CHOH$ |
| 91 | 13 | |
| 120 | 12 | Sn |
| 131 | 15 | |
| 132 | 10 | |
| 133 | 28 | SnMe |
| 134 | 15 | |
| 135 | 35 | |
| 137 | 15 | |
| 141 | 10 | |
| 161 | 35 | |
| 163 | 67 | |
| 164 | 30 | $OSnMe_2$ |
| 165 | 100 | |
| 166 | 10 | |
| 167 | 35 | |
| 297 | 22 | $U + C_4O_3H_x$ |
| 299 | 21 | $U + C_4O_3H_x$ |
| 326 | 11 | |
| 327 | 26 | |
| 328 | 19 | 2U-3Me |
| 330 | 11 | |
| 333 | 10 | |

U = one unit

TABLE 4

| Relative Abundance of $OSnMe_2$ Associated Isotopes. | | |
|---|---|---|
| Sn- | $OSnMe_2$ | % Relative Abundance |
| 116 | 159 | 18.0 |
| 117 | 160 | 7.6 |
| 118 | 161 | 24.0 |
| 119 | 162 | 10.0 |
| 120 | 163 | 33.0 |
| 122 | 165 | 3.4 |
| 124 | 167 | 4.2 |

TABLE 5

| Relative Fragments of SnMe Associated Ion Fragments. | | |
|---|---|---|
| Sn- | SnMe | % Relative Abundance |
| 116 | 131 | 12 |
| 117 | 132 | 8 |
| 118 | 133 | 23 |

TABLE 5-continued

| Relative Fragments of SnMe Associated Ion Fragments. | | |
|---|---|---|
| Sn- | SnMe | % Relative Abundance |
| 119 | 134 | 12 |
| 120 | 135 | 29 |
| 122 | 137 | 11 |
| 124 | 139 | 5 |

EXAMPLE 2

Biological Activity

Bacterial studies were conducted using standard methods for growth inhibition assays. Plates containing a suitable growth medium were seeded with suspensions of the test organism that produced a suitable lawn of test organism after 24 hours incubation at 37° C. Shortly after, the plates were seeded using 1–3 mm square sections of the test material. The bioassays may be run, for example, using 0.1 to 1.0 mg of active ingredients. The plates were incubated and growth inhibition was noted.

The novel compounds, which demonstrated excellent biocidality against *Candida albicans*, were tested using both gram positive (*Staphylococcus aureus*) and gram negative (*Pseudomonas aeruginosa* and/or *E. coli*) organisms, as well as *C. albicans*. These compounds were found to inhibit *Candida albicans* but, had either no inhibitory effect or only a small effect on the other orgainsims tested.

The value of these results lie in the possible manufacture of a cream to eliminate a vaginal yeast infection without destroying the remaining normal flora of the vaginal vault.

TABLE 6

| Biological Properties of Novel Compounds | | | | | |
|---|---|---|---|---|---|
| Tested Material | | Zone of Inhibition (cm) | | | |
| R Groups | Plasticizer | E. coli | P. aeruginosa | S. aureus | C. albicans |
| Me$_2$ | None | NT | 0.2 | 1.0 | 1.5 |
| Me$_2$ | None | 0.5 | 0.7 | 0.7 | Total |
| Me$_2$ | 1 | NT | NI | 0.4 | 2.0 |
| Me$_3$ | None | NT | NI | 0.7 | 2.5 |
| Me$_3$ | None | NI | NI | 0.3 | 1.2 |
| Me$_3$ | 1 | NT | NI | 0.4 | 2.0 |
| Me$_3$ | 1 | NT | NI | 0.4 | 3.0 |
| Me$_3$ | 2 | NI | NI | 0.6 | Total |
| Me$_3$ | 3 | NI | NI | NI | 0.7 |
| Et$_3$ | None | 2.3 | 0.4 | 2.4 | Total |
| Et$_3$ | None | NT | 0.7 | 1.6 | 3.7 |
| Et$_3$ | 1 | 0.9 | 0.4 | 0.8 | Total |
| Et$_3$ | 2 | 1.0 | 0.8 | 1.9 | Total |
| Et$_3$ | 3 | 0.8 | 0.7 | 0.8 | Total |
| Pr$_3$ | None | 0.8 | 0.7 | 3.0 | Total |
| Pr$_3$ | None | NT | 0.6 | 1.8 | Total |
| Pr$_3$ | None | NT | 0.3 | 3.0 | Total |
| Pr$_3$ | 1 | NT | 0.4 | 2.5 | Total |
| Pr$_3$ | 1 | 0.9 | 0.7 | 3.0 | Total |
| Pr$_3$ | 2 | 0.9 | 0.1 | 3.0 | Total |
| Pr$_3$ | 2 | NT | 0.3 | 1.1 | 3.0 |
| Pr$_3$ | 2 | NT | 0.4 | 2.0 | 3.0 |
| Pr$_3$ | 2 | NT | 0.2 | 0.7 | Total |
| Pr$_3$ | 3 | NT | 0.2 | 1.7 | 3.4 |
| Pr$_3$ | 3 | NT | 0.3 | 1.6 | 3.4 |
| Pr$_3$ | 3 | 0.7 | 0.8 | 1.7 | Total |
| Bu$_3$ | None | NT | 0.2 | 4.7 | 3.0 |
| Bu$_3$ | None | Slight | 0.5 | 2.6 | Total |
| Ph$_3$ | None | NI | NI | 0.7 | Total |

Me = Methyl
Et = Ethyl
Pr = Propyl
1 = dialkyl phthalate
2 = isodocyl diphenylphosphate
3 = dioctyl sebocate
NI = no inhibition
NT = not tested
Total = total inhibition

EXAMPLE 3

Formulation and Administration

The compounds of the invention are useful for various non-therapeutic and therapeutic purposes. It is apparent from the testing that the compounds of the invention are effective for inhibiting fungal growth. Because of the antifungal properties of the compounds, they are useful to swab laboratory benches and equipment in a microbiology laboratory to eliminate the presence of fungi. As dislcosed herein, they are also useful prophylactically and therapeutically for treating fungal infections in animals and humans.

The compounds of the subject invention can be used in a variety of applications where microorganisms must be controlled. For example, these compounds can be incorporated into specialty paints, coatings or gloves where they will control fungi and, to a lesser extent, bacteria. As described above, these compounds can be used effectively by women to control yeast infection without upsetting the microfloral balance of the vaginal vault. The compounds may similarly be used to control Candida microbes around wounds.

Therapeutic application of the new compounds and compositions containing them can be contemplated to be accomplished by any suitable therapeutic method and technique presently or prospectively known to those skilled in the art. Further, the compounds of the invention have use as starting materials or intermediates for the preparation of other useful compounds and compositions.

The dosage administration to a host in the above indications will be dependent upon the identity of the infection, the type of host involved, its age, weight, health, kind of concurrent treatment, if any, frequency of treatment, and therapeutic ratio.

The compounds of the subject invention can be formulated according to known methods for preparing pharmaceutically useful compositions. Formulations are described in detail in a number of sources which are well known and readily available to those skilled in the art. For example, *Remington's Pharmaceutical Science* by E. W. Martin describes formulations which can be used in connection with the subject invention. In general, the compositions of the subject invention will be formulated such that an effective amount of the bioactive compound(s) is combined with a suitable carrier in order to facilitate effective administration of the composition.

It should be understood that the examples and embodiments described herein are for illustrative purposes only and that various modifications or changes in light thereof will be suggested to persons skilled in the art and are to be included within the spirit and purview of this application and the scope of the appended claims.

We claim:

1. A compound having the following structural formula:

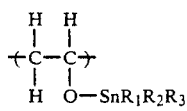

wherein $R_1$, $R_2$, and $R_3$ may be the same or different and are selected from the group consisting of methyl, ethyl, and propyl.

2. The compound, according to claim 1, wherein $R_1$, $R_2$, and $R_3$ are methyl.

3. The compound, according to claim 1, wherein $R_1$, $R_2$, and $R_3$ are ethyl.

4. The compound, according to claim 1, wherein $R_1$, $R_2$, and $R_3$ are propyl.

5. A compound having the following structural formula:

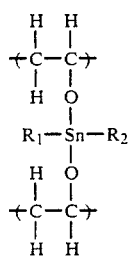

wherein $R_1$ and $R_2$ may be the same or different and are selected from the group consisting of methyl, ethyl, and propyl.

6. The compound, according to claim 5, wherein $R_1$ and $R_2$ are methyl.

7. The compound, according to claim 5, wherein $R_1$ and $R_2$ are ethyl.

8. The compound, according to claim 5, wherein $R_1$ and $R_2$ are propyl.

9. A method for inhibiting the growth of microorganisms, said method comprising the application of a compound having the following structure:

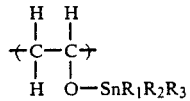

wherein $R_1$, $R_2$, and $R_3$ may be the same or different and are selected from the group consisting of methyl, ethyl, propyl, butyl, and phenyl.

10. The method, according to claim 9, wherein said microorganism is *Candida albicans*.

11. A method for inhibiting the growth of microorganisms, said method comprising the application of a compound having the following structure:

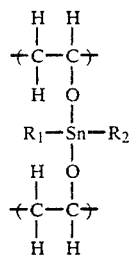

wherein $R_1$ and $R_2$ may be the same or different and are selected from the group consisting of methyl, ehtyl, propyl, butyl, and phenyl.

12. The method, according to claim 11, wherein said microorganism is *Candida albicans*.

13. A pharmaceutical composition comprising an acceptable carrier and one or more compounds with the following structure:

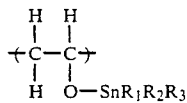

wherein $R_1$, $R_2$, and $R_3$ may be the same or different and are selected from the group consisting of methyl, ethyl, propyl, butyl, and phenyl.

14. A pharmaceutical composition comprising an acceptable carrier and one or more compounds with the following structure:

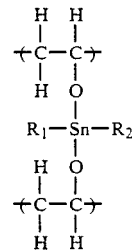

wherein $R_1$ and $R_2$ may be the same or different and are selected from the group consisting of methyl, ethyl, propyl, butyl, and phenyl.

15. A method for preparing a compound having the following structure:

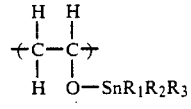

wherein $R_1$, $R_2$, and $R_3$ may be the same or different and are selected from the group consisting of methyl, ethyl, propyl, butyl, and phenyl, said method comprising reacting a solution comprising poly(vinyl alcohol) with a solution comprising an organostannane halide in a largely non-polar solvent in which the organostannane barely dissolves.

16. The method, according to claim 15, wherein said largely non-polar solvent is selected from the group consisting of chloroform and carbon tetrachloride.

* * * * *

UNITED STATES PATENT AND TRADEMARK OFFICE
CERTIFICATE OF CORRECTION

PATENT NO.   : 5,043,463
DATED        : Aug. 27, 1991
INVENTOR(S)  : Charles E. Carraher Jr. and Cynthia Butler It is certified that error appears in the above-identified patent and that said Letters Patent is hereby corrected as shown below:

Title Page:
Item [75]   Inventors: "Cindy Butler" should read --Cynthia Butler--
Column 4:   lines 33-37 " 120  12  ]  Sn"   should read -- 120  12       Sn
                         131  15  |                      131  15  ]
                         132  10  |                      132  10  |
                         133  28  }  SnMe                133  28  }  SnMe
                         134  15  |                      134  15  |
                         135  35  ]                      135  35  |
                         137  15"                        137  15  ]--

Signed and Sealed this

Sixth Day of April, 1993

Attest:

STEPHEN G. KUNIN

Attesting Officer    Acting Commissioner of Patents and Trademarks